United States Patent [19]

Nagabhushan

[11] 3,997,524
[45] Dec. 14, 1976

[54] PROCESS FOR THE MANUFACTURE OF 6'-N-ALKYL DERIVATIVES OF SISOMICIN AND VERDAMICIN; NOVEL INTERMEDIATES USEFUL THEREIN, AND NOVEL 6'-N-ALKYLVERDAMICINS PREPARED THEREBY

[75] Inventor: Tattanahalli Lakshminarayan Nagabhushan, Parsippany, N.J.

[73] Assignee: Schering Corporation, Kenilworth, N.J.

[22] Filed: May 2, 1975

[21] Appl. No.: 574,072

[52] U.S. Cl. .................................. 536/17; 424/180
[51] Int. Cl.² ......................................... C07H 15/22
[58] Field of Search ..... 260/210 AB, 210 K, 210 R

[56] References Cited
UNITED STATES PATENTS 3,832,286  8/1974  Weinstein et al. .......... 260/210 AB
3,925,353  12/1975  Umezawa et al. ........... 260/210 AB

FOREIGN PATENTS OR APPLICATIONS 1,033,394  6/1966  United Kingdom ......... 260/210 NE

*Primary Examiner*—Johnnie R. Brown
*Attorney, Agent, or Firm*—Mary S. King

[57] ABSTRACT

1,3,2',3''-tetra-N-acyl-5'-deaminomethyl-5'-formyl-sisomicin and 1,3,2',3''-tetra-N-acyl-5'-de-α-aminoethyl-5'-acetylverdamicin are prepared from the 1,3,2',3''-tetra-N-acyl-6'-N-(2,4-dinitrophenyl) derivatives of sisomicin and verdamicin, respectively, by reaction with selenium dioxide. They are useful intermediates in the preparation of 6'-N-alkylsisomicin derivatives and 6'-N-alkylverdamicin derivatives having antibacterial activity.

9 Claims, No Drawings

PROCESS FOR THE MANUFACTURE OF 6'-N-ALKYL DERIVATIVES OF SISOMICIN AND VERDAMICIN; NOVEL INTERMEDIATES USEFUL THEREIN, AND NOVEL 6'-N-ALKYLVERDAMICINS PREPARED THEREBY

FIELD OF THE INVENTION

This invention relates to novel compositions of matter, to methods for their manufacture and to methods for their use in the manufacture of known antibiotics and of novel antibacterial agents.

More specifically, this invention relates to 1,3,2',3''-tetra-N-acyl-5'-deaminomethyl-5'-formylsisomicin and to 1,3,2',3''-tetra-N-acyl-5'-de-α-aminoethyl-5'-acetylverdamicin, to the methods for their manufacture, and to their use as intermediates in the manufacture of known antibiotics and novel antibacterial agents.

In particular, this invention relates to 1,3,2',3''-tetra-N-lower alkanoyl-5'-deaminomethyl-5'-formylsisomicin and 1,3,2',3''-tetra-N-lower alkanoyl-5'-de-α-aminoethyl-5'-acetylverdamicin and their conversion to 6'-N-alkylsisomicin derivatives and to novel 6'-N-alkylverdamicin derivatives having antibacterial activity.

The 6'-N-alkylsisomicin antibacterial agents are described and claimed in copending application Ser. No. 574,070 filed May 2, 1975, now abandoned, of Peter J. L. Daniels and William N. Turner for 6'-N-ALKYL-4,6-DI-O-(AMINOGLYCOSYL)-1,3-DIAMINOCYCLITOLS, METHODS FOR THEIR MANUFACTURE AND INTERMEDIATES USEFUL THEREIN, METHODS FOR THEIR USE AS ANTIBACTERIAL AGENTS AND COMPOSITIONS USEFUL THEREFORE.

PRIOR ART

Sisomicin and verdamicin are known antibiotics prepared by the fermentation of *Micromonospora inyoensis* and *Micromonospora grisea*, respectively. By my invention, novel intermediates of sisomicin and verdamicin are prepared which are easily converted to 6'-N-alkyl derivatives of sisomicin and verdamicin having antibacterial activity.

GENERAL DESCRIPTION OF THE INVENTION COMPOSITION-OF-MATTER ASPECT

One of the composition-of-matter aspects of this invention relates to novel compounds represented by the formula I:

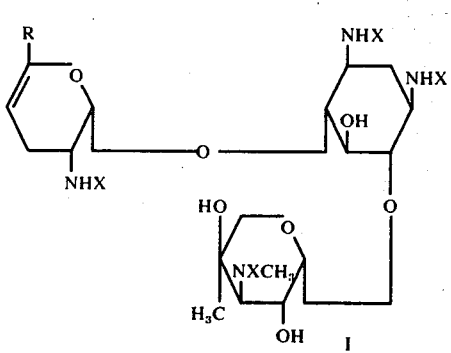

wherein X is a member selected from the group consisting of lower alkanoyl, benzoyl, substituted benzoyl, lower alkoxycarbonyl, chloroacetyl and trichloroethoxycarbonyl; and R is —CHO or —COCH$_3$.

In formula I;
by "lower alkanoyl" are included "X" radicals having up to eight carbon atoms such as formyl, acetyl, propionyl, valeryl, caproyl and caproyl;
by "substituted benzoyl" are included "X" radicals wherein benzoyl is substituted by methyl, methoxy and nitro groups;
by "lower alkoxycarbonyl" are included "X" radicals having up to 8 carbon atoms, e.g. methoxycarbonyl, ethoxycarbonyl, n-propyloxycarbonyl, isopropyloxycarbonyl, n-butoxycarbonyl, tert-butoxycarbonyl, tert-amyloxycarbonyl, octyloxycarbonyl.

The compounds of formula I are useful as intermediates in preparing antibacterially active 6'-N-alkylsisomicin and 6'-N-alkylverdamicin derivatives by the process of this invention as described hereinbelow.

The compound of formula I wherein R is -CHO and X is acetyl may be named as 4-O-(2'-acetamido-6'-aldehydo-2',3',4'-trideoxy-α-D-glycero-hex-4'-enopyranosyl)-tri-N-acetyl garamine or, alternatively as 1,3,2',3''-tetra-N-acetyl-5'-deaminomethyl-5'-formylsisomicin.

Similarly, the compound of formula I wherein R is —COCH$_3$ and X is acetyl may be named as 4-O-(2'-acetamido-2',3',4',7'-tetradeoxy-α-D-glycero-hept-4'-enopyranos-6'-ulosyl)-tri-N-acetyl garamine or, alternatively, as 1,3,2'3''-tetra-N-acetyl-5'-de-α-aminoethyl-5'-acetylverdamicin.

In this application the latter system of nomenclature will be used for these compounds of the invention.

The 1,3,2',3''-tetra-N-X-5'-deaminomethyl-5'-formylsisomicin and 1,3,2',3''-tetra-N-X-5'-de-α-aminoethyl-5'-acetylverdamicin of this invention are characterized as colorless amorphous solids.

Another composition-of-matter aspect of my invention includes compounds of formula I where R is —CH$_2$NHW or

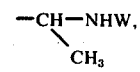

W being 2,4-dinitrophenyl, said compounds being useful as intermediates in the preparation of compounds of formula I wherein R is —CHO or —COCH$_3$. Compounds of this aspect of my invention wherein X is acetyl and W is as stated hereinabove include a. when R is —CH$_2$NHW; 1,3,2',3''-tetra-N-acetyl-6'-N-(2,4-dinitrophenyl)sisomicin,
b. when R is

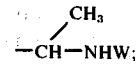

1,3,2',3''-tetra-N-acetyl-6'-N-(2,4-dinitrophenyl)-verdamicin,

The 1,3,2',3''-tetra-N-X-6'-N-(2,4-dinitrophenyl)-sisomicin and 1,3,2',3''-tetra-N-X-6'-N-(2,4-dinitrophenyl)verdamicin of this invention are characterized as yellow amorphous solids.

In another composition-of-matter aspect, this invention relates to novel 6'-N-alkylverdamicin derivatives represented by the following formula II:

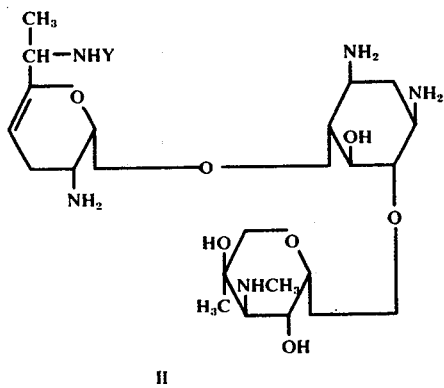

II wherein Y is an alkyl substituent selected from the group consisting of alkyl, alkenyl, cycloalkyl, hydroxyalkyl, aminoalkyl, alkylaminoalkyl, aminohydroxyalkyl and alkylaminohydroxyalkyl, said alkyl substituent having up to 8 carbon atoms. When said alkyl substituent is substituted by both hydroxyl and amino functions, only one of said functions can be attached at any one carbon atom. This invention also includes the pharmaceutically acceptable acid addition salts of the 6'-N-alkyl derivatives of formula II.

The 6'-N-alkylverdamicin derivatives of this invention are characterized as colorless, amorphous solids.

The acid addition salts of 6'-N-alkylverdamicin derivatives are prepared according to known procedures such as by neutralizing the free base with the appropriate acid, usually to about pH 5. Suitable acids for this purpose include acids such as hydrochloric, sulfuric, phosphoric, hydrobromic and the like.

The acid addition salts of the 6'-N-alkylverdamicin derivatives are characterized by being white solids which are soluble in water and sparingly soluble in most polar and non-polar organic solvents.

The 6'-N-alkylverdamicin derivatives of this invention and their non-toxic pharmaceutically acceptable acid addition salts, in general, exhibit anti-bacterial activity and usually have a spectrum of activity similar to that of the parent antibiotic. Thus the compounds of my invention are broad spectrum antibacterial agents being active against gram positive and gram negative bacteria and therefore, can be used alone or in combination with other antibiotic agents to prevent the growth or reduce the number of bacteria in various environments.

The 6'-N-alkylverdamicins and their non-toxic pharmaceutically acceptable acid addition salts, with a compatible pharmaceutically acceptable carrier or coating may be administered in a dose dependent upon the age and weight of the animal species being treated, the mode of administration, and the type and severity of bacterial infection being prevented or reduced. My compounds may also be used, for example, to disinfect laboratory glassware, dental and medical equipment.

PROCESS ASPECT OF THE INVENTION

One process of this invention relates to the preparation of 6'-N-Y-sisomicins or 6'-N-Y-verdamicins wherein Y is an alkyl substituent selected from the group consisting of alkyl, alkenyl, cycloalkyl, hydroxyalkyl, aminoalkyl, alkylaminoalkyl, aminohydroxyalkyl and alkylaminohydroxyalkyl, said alkyl substituent having up to 8 carbon atoms and when said alkyl substituent is substituted by both hydroxy and amino functions only one of said functions can be attached at any one carbon atom.

This process, whereby the 6'-N-Y-sisomicins or 6'-N-Y-verdamicins are prepared, comprises the reaction of 1,3,2',3''-tetra-N-X-5'-deaminomethyl-5'-formylsisomicin or 1,3,2',3''-tetra-N-X-5'-de-α-aminoethyl-5'-acetylverdamicin, respectively, wherein X is as defined hereinabove in formula I, in a protic solvent with a primary amine having the formula Y—NH$_2$, wherein Y is as hereinabove defined, with a hydride donor reducing agent, followed by the reaction of the thereby formed N-protected-6'-N-Y-sisomicin or N-protected 6'-N-Y-verdamicin intermediates with base to obtain 6'-N-Y-sisomicins or 6'-N-Y-verdamicins, respectively.

Protic solvents useful in my process include lower alkanols, aqueous tetrahydrofuran, aqueous dioxane or water, preferably a mixture of a lower alkanol and water.

Hydride donor reducing agents useful in my process are selected from the group consisting of sodium borohydride, lithium borohydride, potassium borohydride, lithium cyanoborohydride, sodium cyanoborohydride, morpholinoborane, dialkylaminoborane and tetraalkylammonium cyanoborohydride.

My process is usually carried out at room temperature utilizing about a 5–10 molar excess of a primary amine. However, my process can be carried out in the temperature range of −20° to 50° C utilizing a 1–10 molar excess of a primary amine.

When removing the protecting groups from the N-protected-6'-N-Y-sisomicin intermediates or N-protected-6'-N-Y-verdamicin intermediates, I usually utilize a base, for example, sodium hydroxide or potassium hydroxide at elevated temperatures, about 100° C under an atmosphere of nitrogen.

By my process, when 1,3,2',3'-tetra-N-acetyl-5'-deaminomethyl-5'-formylsisomicin is treated with, for example, methylamine or 2-phenethylamine, there is obtained Antibiotic G-52 and 6'-N-(2-phenylethyl)-sisomicin, respectively. Similarly, when 1,3,2',3''-tetra-N-acetyl-5'-de-α-aminoethyl-5'-acetylverdamicin is treated with ethylamine or 1,4-diaminobutane there is obtained 6'-N-ethylverdamicin and 6'-N-(δ-aminobutyl) verdamicin, respectively.

When carrying out my process utilizing the primary amine (Y—NH$_2$) wherein the alkyl substituent Y is an amino alkyl, the amine groups need not be protected prior to reaction with the intermediates of my invention, so long as said amine groups are symmetrically positioned on the alkyl moiety. However, when the primary amine Y—NH$_2$ has an alkyl substituent Y wherein the Y group is an aminohydroxyalkyl or a hydroxy alkyl, one of said amine groups is preferably protected if the amine groups are not in symmetrical relationship to one another and/or to the hydroxy group prior to reaction with the intermediates of my invention. The hydroxyl functions of these reactants may be protected, although this is not necessary. For example, when preparing 6'-N-(δ-aminobutyl)sisomicin or the corresponding verdamicin derivative, the starting material is 1,4-diaminobutane. However, when preparing 6'-N-(β-hydroxy-δ aminobutyl)sisomicin or the corresponding verdamicin derivative, the requisite starting compound is 4-acetamido-2-acetoxybutylamine, which is prepared by treating 4,4-diethoxy-3-hydroxybutylamine with acetic anhydride, hydrolyzing the resultant 4,4-diethoxy-3-acetoxy-1-acetamidobutane and subjecting the thereby formed 4-acetamido-2-acetoxybutanal to reductive amination to obtain 4-acetamido-2acetoxybutylamine. Reaction of the foregoing intermediate with 1,3,2',3''-tetra-N-acetyl-5'-deaminomethyl-5'-formylsisomicin or 1,3,2',3''-tetra-N-acetyl-5'-de-α-aminoethyl-5'-acetylverdamicin cin with a hydride donor reducing agent followed by removal of the N-protected groups by my process will produce 6'-N-(β-hydroxy-δ-aminobutyl)sisomicin or 6'-N-(β-hydroxy-δ-aminobutyl)verdamicin, respectively.

In carrying out my process if, instead of a primary amine such as Y—NH$_2$, ammonia is reacted with either 1,3,2',3''-tetra-N-acetyl-5'-deaminomethyl-5'-formylsisomicin or 1,3,2',3''-tetra-N-acetyl-5'-de-α-aminoethyl-5'-acetylverdamicin, there is then produced sisomicin or verdamicin, respectively.

The novel requisite intermediates of my invention, i.e. 1,3,2',3''-tetra-N-X-5'-deaminomethyl-5'-formylsisomicin and 1,3,2',3''-tetra-N-X-5'-de-α-aminoethyl-5'-acetylverdamicin are conveniently prepared by the reaction of 1,3,2',3''-tetra-N-X-6'-(2,4-dinitrophenyl)-sisomicin or 1,3,2',3''-tetra-N-X-6'-(2,4-dinitrophenyl verdamicin, respectively, wherein X is as defined in formula I, with selenium dioxide in water, usually at room temperatures. Although the conditions above are preferred, other oxidizing agents, for example manganese dioxide, potassium permanganate (buffered with calcium sulfate) in an aqueous or aqueous alkanol system, and chromic anhydride in aqueous acetic acid or pyridine and water may be used. The reaction temperature may be in the range of from about 10° C to about 50° C.

In turn, the 1,3,2',3''-tetra-N-X-6''-(2,4-dinitrophenyl)sisomicin or 1,3,2',3''-tetra-N-X-6'-(2,4dinitrophenyl)verdamicin precursor intermediates of this invention are prepared, for example, from the 6'-N-trifluoroacetyl derivatives of sisomicin or verdamicin, by introducing "X" protecting groups via methods similar to those known in the art onto the 1,3,2',3''-tetra amine functions, then removing the 6'-N-trifluoroacetyl group with weak base to form 1,3,2',3''tetra-N-X-sisomicin or 1,3,2',3''-tetra-N-X verdamicin which, when reacted with 2,4-dinitrofluorobenzene, yields 1,3,2',3''-tetra-N-X-6'-N-(2,4-dinitrophenyl)sisomicin or 1,3,2',3''-tetra-N-X-6'-N-(2,4-dinitrophenyl)verdamicin, respectively.

In this process, the 1,3,2',3''-tetra-N-acetyl derivatives of 6'-N-trifluoroacetyl sisomicin and verdamicin are prepared as intermediates from the 6'-N-trifluoroacetyl sisomicin or verdamicin by reaction with acetic anhydride in methanol. Other useful 1,3,2',3''-N-protecting groups include other lower alkanoyl derivatives, for example, propionyl, caprylyl, benzoyl and substituted benzoyl (e.g. o, m, or p-nitrobenzoyl; o, m, or p-methoxybenzoyl and o, m or p-toluyl) which are also prepared from their corresponding anhydrides in methanol or aqueous methanol, from their corresponding acid chlorides in the aforementioned solvents in the presence of a base or pyridine. Still other useful protecting groups for positions 1,3,2',3'' are the lower alkoxy carbonyls, for example, t-butoxy carbonyl and t-amyloxycarbonyl, which are prepared from their corresponding azides in the presence of triethylamine and aqueous methanol. Another particularly useful protecting group for positions 1,3,2',3'' is trichloroethoxycarbonyl which is derived from trichloroethoxycarbonyl-N-hydroxysuccinimide in the presence of triethylamine and aqueous methanol.

The invention described hereinabove is illustrated in detail hereinbelow in the Preparations and Examples which should not be construed as limiting the scope of my invention.

PREPARATION OF INTERMEDIATES

PREPARATION 1

A. 6'-N-Trifluoroacetylsisomicin

Dissolve 45 gms. of sisomicin (100.6 mmoles) in 1100 ml. of methanol, slowly add over a period of 10–30 minutes with stirring a solution of 13.5 ml. of ethyltrifluorothiolacetate (105 mmoles, 1.05 equivalents) in 75 ml. of methanol. Stir the solution at room temperature for an additional period of ½ to 2 hours, then evaporate in vacuo to a residue comprising 6'-N-trifluoroacetylsisomicin.

B. 6'-N-Trifluoroacetylverdamicin

In above Preparation 1A, use as starting material an equivalent quantity of verdamicin to obtain a product comprising 6'-N-trifluoroacetylverdamicin.

PREPARATION 2

A.
1,3,2',3''-Tetra-N-acetyl-6'-N-trifluoroacetylsisomicin

Dissolve the 6'-N-trifluoroacetylsisomicin prepared as described in Preparation 1A in 900 ml. of methanol. Cool the solution to about −4° C, then add with stirring 67.5 ml. of acetic anhydride (715 mmoles, 7.05 equivalents). Stir the solution at room temperature for a period of from about 2 to 18 hours until the reaction is complete as determined by thin layer chromatography. Evaporate the solution in vacuo to a residue comprising 1,3,2',3''-tetra-N-acetyl-6'-N-trifluoroacetylsisomicin.

B.
1,3,2',3''-Tetra-N-acetyl-6'-N-trifluoroacetylverdamicin

In above Preparation 2A use as starting material an equivalent quantity of the product of Preparation 1B to obtain a product comprising 1,3,2',3''-tetra-N-acetyl-6'-N-trifluoroacetylverdamicin.

C.
1,3,2',3''-Tetra-N-acyl-6'-N-trifluoroacetylsisomicin or Verdamicin

1. In a manner similar to that described in Preparation 2A and 2B react 6'-N-trifluoroacetylsisomicin or verdamicin, respectively, with each of the following anhydrides:
    a. formic acetic anhydride
    b. caprylic anhydride
    c. benzoic anhydride
    d. chloroacetic anhydride
and isolate the resultant 1,3,2',3''-tetra-N-protected-6'-N-trifluoroacetyl sisomicin or verdamicin compounds, respectively:
    e.     1,3,2',3''-tetra-N-formyl-6'-N-trifluoracetylsisomicin or verdamicin
    f.     1,3,2',3''-tetra-N-capryl-6'-N-trifluoroacetylsisomicin or verdamicin
    g.     1,3,2',3''-tetra-N-benzoyl-6'-N-trifluoroacetylsisomicin or verdamicin
    h.     1,3,2',3''-tetra-N-chloroacetyl-6'-N-trifluoroacetylsisomicin or verdamicin

2. To a stirred solution of 6'-N-trifluoroacetylsisomicin (6 mmoles) in 50% aqueous methanol containing triethylamine (3.64 ml.), cooled to 5° C add t-butoxycarbonyl azide (26 mmoles). Stir the reaction mixture for 18 hours at 5° C then add Amberlite IRA-401S ion exchange resin (OH⁻ cycle), and continue stirring for an additional 30 minutes. Remove the resin by filtration, concentrate the filtrate in vacuo, chromatograph the resultant residue over silica gel using the lower phase of a 2:1:1, chloroform:methanol:concentrated ammonium hydroxide solvent system. Monitor the fractions by thin layer chromatography and combine those containing the pure major product and lyophilize to a residue of 1,3,2', 3''-tetra-N-t-butoxycarbonyl-6'-N-trifluoroacetylsisomicin.

In a manner similar to that descirbed in Preparation 2-C-2 react 6'-N-trifluoroacetylverdamicin with t-butoxycarbonyl azide to obtain 1,3,2',3''-tetra-N-t-butoxycarbonyl-6'-N-trifluoroacetylverdamicin.

Further, in a manner similar to that described in Preparation 2-C-2, react 6'-N-trifluoroacetylsisomicin or verdamicin with trichloroethoxycarbonyl-N-hydroxysuccinimide instead of with t-butoxycarbonyl azide to obtain 1,3,2',3''-tetra-N-trichloroethoxycarbonyl-6'-N-trifluoroacetylsisomicin or 1,3,2',3''-tetra-N-trichloroethoxycarbonyl-6'-N-trifluoroacetylverdamicin respectively.

PREPARATION 3

A. 1,3,2',3''-Tetra-N-acetylsisomicin

Dissolve the 1,3,2',3''-tetra-N-acetyl-6'-N-trifluoroacetylsisomicin prepared as described in Preparation 2A in methanol. Add 500 ml. of 28% aqueous ammonium hydroxide and allow the solution to stand at room temperature overnight. Evaporate the solution in vacuo to a residue comprising 1,3,2',3''-tetra-N-acetylsisomicin. Purify by chromatographing on silica gel eluting with a solvent mixture comprising chloroform:methanol:14% ammonium hydroxide (27.7:6:1), taking 20 ml. fractions. Monitor the eluted fractions via thin layer chromatography using the lower phase of chloroform:methanol:28% ammonium hydroxide (1:1:1). Combine the fractions containing 1,3,2',3''-tetra-N-acetylsisomicin as determined by thin layer chromatography, evaporate in vacuo to a residue of 1,3,2',3''-tetra-N-acetylsisomicin having the following physical constants: $[\alpha]_D^{26} + 207.4°$ (c, 0.3, H$_2$O); characteristic and mass spectral peaks at m/e 615 (M .+), 598, 443, 425, 415, 397, 275, 257, 247, 229, 202, 169; pmr peaks (60 MHz, D$_2$O) at δ 1.07, 1.17 (3H, C-Me rotamers), 1.95, 1.98, 2.03 (12H, NCOMe), 3.13, 3.00 (3H, N-Me rotamers), 5.29 (1H, d, J=4Hz, H-1''), 5.64 (1H, d, J=2.5Hz, H-1')ppm.

B. 1,3,2',3''-Tetra-N-acetylverdamicin

In above Preparation 3A use as starting material an equivalent quantity of the product of Preparation 2B to obtain 1,3,2',3''-tetra-N-acetylverdamicin.

C. 1,3,2',3''-Tetra-N-acylsisomicin or Verdamicin

In a manner similar to that described in Preparation 3A and 3B react the products of Preparations 2-C-1 and 2-C-2 with weak base and isolate the resultant products to obtain respectively:

a. 1,3,2',3''-tetra-N-formylsisomicin or verdamicin
b. 1,3,2',3''-tetra-N-caprylsisomicin or verdamicin
c. 1,3,2',3''-tetra-N-benzoylsisomicin or verdamicin
d. 1,3,2',3''-tetra-N-chloroacetylsisomicin or verdamicin
e. 1,3,2',3''-tetra-N-t-butoxycarbonylsisomicin or verdamicin
f. 1,3,2',3''-tetra-N-trichloroethoxycarbonylsisomicin or verdamicin.

PREPARATION 4

4-Acetamido-2-acetoxybutylamine

Treat 4,4-diethoxy-3-hydroxybutylamine with acetic anhydride in pyridine to obtain 4,4-diethoxy-3-acetoxy-1-acetamido butane. Hydrolyze with 1N aqueous sulfuric acid at 25° C to obtain 4-acetamido-2-acetoxybutanal. Subject to reductive amination in aqueous methanol using ammonium chloride and sodium cyanoborohydride at 25° C to obtain 4-acetamido-2-acetoxybutylamine.

PREPARATION 5

4-(N-Methylacetamido)-2-acetoxybutylamine

Treat 4,4-diethoxy-3-hydroxybutylamine with acetic anhydride in pyridine to obtain 4,4-diethoxy-3-acetoxy-1-acetamido butane. Treat with sodium hydride and methyl iodide to obtain 1-(N-methylacetamido)-3-acetoxy-4,4-diethoxybutane. Hydrolyze the resultant 1-(N-methylacetamido)-3-acetoxy-4,4-diethoxybutane with 1N sulfuric acid at 25° C then reductively aminate the resulting 4-(N-methylacetamido)-2-acetoxybutanal to obtain the resulting 4-(N-methylacetamido)-2-acetoxy-butylamine.

EXAMPLES

EXAMPLE I

A. 1,3,2',3''-Tetra-N-acetyl-6'-N-(2,4-dinitrophenyl)-sisomicin

Add 2.9 ml. of 2,4-dinitrofluorobenzene to a stirred mixture of 6.15 g. of 1,3,2',3''-tetra-N-acetylsisomicin, 2.5 g of sodium carbonate, 50 ml. of methanol and 15 ml. of water. Stir the mixture for 18 hours at room temperature and then remove the solvents in vacuo. Chromatograph the resultant residue on 500 g. silica gel eluting with a solvent mixture comprising the bottom phase of 2:1:1 mixture of chloroform, methanol and ammonium hydroxide. Pool the eluted fractions containing the major product, concentrate and lyophilize to give 5.8 g of 1,3,2',3''-tetra-N-acetyl-6'-N-(2,4-dinitrophenyl)sisomicin; $[\alpha]_D^{26} + 133.3°$ (c, 0.4 in water) NMR (100 MHz, D$_2$O, DSS): δ 1.02 ppm, 1.14 (c-methyl), 1.98, 1.94, 2.20 (N-acetyls), 2.98, 3.12 (N-methyl), 5.0 (H-4'-broadish triplet), 5.28 (H-1'', J$_1''$,$_2'$=4.0 Hz), 5.56 (H-1', J$_1'$, $_2'$=2.5Hz), 7.10 (H-6''', J$_5'''$, $_6'''$=10 Hz), 8.20 (H-5'''), 8.86 (H-3''').

B. 1,3,2',3''-Tetra-N-acetyl-6'-N-(2,4-dinitrophenyl)verdamicin

In a similar manner, subject to the process described in Example 1A an equivalent quantity of 1,3,2',3''-tetra-N-acetylverdamicin and isolate the resultant product to obtain 1,3,2',3''-tetra-N-acetyl-6'-N-(2,4-dinitrophenyl)verdamicin.

C.
1,3,2',3''-Tetra-N-acyl-6'-N-(2,4-dinitrophenyl)-sisomicin or Verdamicin In a manner similar to that described in Examples IA and IB react the products of Preparation 3C with 2,4-dinitrofluorobenzene, sodium carbonate and aqueous alkanol to obtain the resultant products:

a. 1,3,2',3''-tetra-N-formyl-6'-N-(2,4-dinitrophenyl)-sisomicin
b. 1,3,2',3''-tetra-N-formyl-6'-N-(2,4-dinitrophenyl)-verdamicin
c. 1,3,2',3''-tetra-N-capryl-6'-N-(2,4-dinitrophenyl)-sisomicin
d. 1,3,2',3''-tetra-N-capryl-6'-N-(2,4-dinitrophenyl)-verdamicin
e. 1,3,2',3''-tetra-N-benzoyl-6'-N-(2,4-dinitrophenyl)-sisomicin
f. 1,3,2',3''-tetra-N-benzoyl-6'-N-(2,4-dinitrophenyl)-verdamicin
g. 1,3,2',3''-tetra-N-chloroacetyl-6'-N-(2,4-dinitrophenyl)sisomicin
h. 1,3,2',3''-tetra-N-chloroacetyl-6'-N-(2,4-dinitrophenyl)verdamicin
i. 1,3,2',3''-tetra-N-t-butoxycarbonyl-6'-N-(2,4-dinitrophenyl)sisomicin
j. 1,3,2',3''-tetra-N-t-butoxycarbonyl-6'-N-(2,4-dinitrophenyl)verdamicin
k. 1,3,2',3''-tetra-N-trichloroethoxycarbonyl-6'-N-(2,4-dinitrophenyl)sisomicin.
l. 1,3,2',3''-tetra-N-trichloroethoxycarbonyl-6'-N-(2,4-dinitrophenyl)verdamicin.

EXAMPLE 2
A.
1,3,2',3''-Tetra-N-acetyl-5'-deaminomethyl-5'-formylsisomicin Add 0.45 g. of selenium dioxide to a stirred solution of 0.78 g. of 1,3,2',3''-tetra-N-acetyl-6'-N-(2,4-dinitrophenyl)sisomicin in water. Continue stirring at room temperature for 5 days. Filter the solution and concentrate the filtrate to dryness in vacuo. Chromatograph the resultant residue on 50 g. silica gel using the lower phase of a 2:1:1 mixture of chloroform:methanol:ammonium hydoxide in a column of 3 cm. diameter.

Pool the eluted fractions, concentrate in vacuo and lyophilize to give 0.37 g. of 1,2,3',3''-tetra-N-acetyl-5'-deaminomethyl-5'-formylsisomicin $[\alpha]_D^{26}$ + 195.8° (c, 0.4 in water); NMR (100 MHz, D$_2$O, DSS: δ 1.16 ppm. 1.06 (c-methyl), 1.84, 1.98, 2.04, 2.22 (N-acetyls), 3.0, 3.14 (N-methyl), 4.71 (H-5''eq, J$_5$''eq, ax=11.25Hz), 5.30 (H-1''', J$_1$''$_{,2}$''=3.5Hz), 5.70 (H-1', J$_1$'$_{,2}$'=2.5Hz), 6.40 (H-4', triplet, J=~ 3.5Hz), 9.22 (CHO).

B.
1,3,2'3''-Tetra-N-acyl-5'-deaminomethyl-5'-formylsisomicin

In a similar manner, subject to the process described in Example 2A, an equivalent quantity of the products of Example 1C a,c,e,g,i and k, and isolate the resultant products to obtain, respectively:

a. 1,3,2',3''-tetra-N-formyl-5'-deaminomethyl-5''-formylsisomicin
b. 1,3,2',3''-tetra-N-capryl-5'-deaminomethyl-5'-formylsisomicin
c. 1,3,2',3''-tetra-N-benzoyl-5'-deaminomethyl-5'-formylsisomicin
d. 1,3,2',3''-tetra-N-chloroacetyl-5'-deaminomethyl-5'-formylsisomicin
e. 1,3,2',3''-tetra-N-t-butoxycarbonyl-5'-deaminomethyl-5'-formylsisomicin
f. 1,3,2',3''-tetra-N-trichloroethoxycarbonyl-5'-deaminomethyl-5'-formylsisomicin.

C.
1,3,2',3''-Tetra-N-acetyl-5'-De-α-aminoethyl-5'-acetylverdamicin

In a similar manner, subject to the process described in Example 2A an equivalent quantity of 1,3,2',3''-tetra-N-acetyl-6'-N-(2,4-dinitrophenyl)verdamicin and isolate the resultant product to obtain 1,3,2',3''-tetra-N-acetyl-5'-de-α-aminoethyl-5'-acetylverdamicin.

D.
1,3,2',3''-Tetra-N-acyl-5'-de-α-aminoethyl-5'-acetylverdamicin

In a similar manner, subject to the process described in Example 2A an equivalent quantity of the products of Example 1C b,d,f,h,j, and l, and isolate the resultant products to obtain, respectively:

a. 1,3,2',3''-tetra-N-formyl-5'-de-α-aminoethyl-5'-acetylverdamicin
b. 1,3,2',3''-tetra-N-capryl-5'-de-α-aminoethyl-5'-acetylverdamicin
c. 1,3,2',3''-tetra-N-benzoyl-5'-de-α-aminoethyl-5'-acetylverdamicin
d. 1,3,2',3''-tetra-N-chloroacetyl-5'-de-α-aminoethyl-5'-acetylverdamicin
e. 1,3,2',3''-tetra-N-t-butoxycarbonyl-5'-de-α-aminoethyl-5'-acetylverdamicin
f. 1,3,2',3''-tetra-N-trichloroethoxycarbonyl-5'-de-α-aminoethyl-5'-acetylverdamicin.

EXAMPLE 3
Antibiotic G-52

Dissolve 0.2 gm. of 1,3,2',3''-tetra-N-acetyl-5'-deaminomethyl-5'-formylsisomicin in a mixture of 5 ml. of methanol and 5 ml. of water. Bubble gaseous methylamine into the stirred solution for 15 minutes. Add 24 mg. of sodium borohydride to the solution and continue stirring for 30 minutes. Concentrate the solution to dryness in vacuo and dissolve the residue in 10 ml. of 1N sodium hydroxide. Reflux the solution under nitrogen for 48 hours. Cool the solution and pass through 40 ml. of Amberlite IRC-50 ion exchange resin in the ammonium form and wash with water. Elute the product with 3% ammonium hydroxide solution and concentrate the eluate. Chromatograph the residue on 20 g. silica gel using a system consisting of chloroform (30), methanol (10) and ammonium hydroxide(1). Pool the homogeneous fractions, concentrate and lyophilize to give Antibiotic G-52.

EXAMPLE 4
6'-N-(2-Phenylethyl)-sisomicin

Dissolve 500 mg. of 1,3,2',3''-tetra-N-acetyl-5'-deaminomethyl-5'-formylsisomicin in a solution of 7 ml. of 2-phenylethylamine and 3.5 ml. of ethanol and 3.5 ml. of water. Stir the solution for 10 minutes, add 24 mg. of sodium borohydride and continue stirring for 30 minutes. Concentrate the solution to dryness in vacuo and dissolve the resultant residue in 20 ml. of 1N sodium hydroxide. Reflux the solution under nitrogen for 48 hours. Cool the solution and pass through 40 ml. of Amberlite IRC-50 ion exchange resin in the ammonium form and wash with water. Elute the product with 3% ammonium hydroxide solution and concentrate the eluate. Chromatograph the residue on 20 gm. silica gel using the system chloroform:methanol:ammonium hydroxide, 30:10:1.

Pool the homogeneous fractions as determined by thin layer chromatography, concentrate and lyophilize to obtain 6'-N-(2-phenylethyl)sisomicin.

EXAMPLE 5

6'-N-Alkylsisomicins

1. In a manner similar to that described in Example 4 react 1,3,2',3''-tetra-N-acetyl-5'-deaminomethyl-5'-formylsisomicin with an excess quantity of each of the following amines:

a. ethylamine
b. isopropylamine
c. cyclopropylmethylamine
d. ethanolamine
e. allylamine
f. 1,4-diaminobutane
g. 4-acetamido-2-acetoxybutylamine
h. 4-(N-methylacetamido)-2-acetoxybutylamine and isolate the resultant products to obtain respectively:

i. 6'-N-ethylsisomicin
j. 6'-N-isopropylsisomicin
k. 6'-N-cyclopropylmethylsisomicin
l. 6'-N-(β-hydroxyethyl)sisomicin
m. 6'-N-allylsisomicin
n. 6'-N-(δ-aminobutyl)sisomicin
o. 6'-N-(β-hydroxy- δ-aminobutyl)sisomicin
p. 6'-N-[β-hydroxy- δ-(methylamino)butyl]-sisomicin 2. In a manner similar to that described in Example 4 react the 1,3,2',3''-tetra-N-acyl-5'-deaminomethyl-5'-formylsisomicins of Example 2B with an excess quantity of the amines of Example 5, a–h to isolate the products of Example 5, i–p.

EXAMPLE 6

6'-N-Ethylverdamicin

Dissolve 0.2 gms. of 1,3,2',3''-tetra-N-acetyl-5'-de-α-aminoethyl-5'-acetylverdamicin in a mixture of 5 ml. of ethanol, 5 ml. of water and 5 ml. of ethylamine. Stir the solution for 10 minutes, add 24 mg. of sodium borohydride and continue stirring for 30 minutes. Concentrate the solution to dryness in vacuo and dissolve the resultant residue in 20 ml. of 1N sodium hydroxide. Reflux the solution under nitrogen for 48 hours. Cool the solution and pass through 40 ml. of Amberlite IRC-50 ion exchange resin in the ammonium form and wash with water. Elute the product with 3% ammonium hydroxide solution and concentrate the eluate. Chromatograph the residue on 20 gm. silica gel using the system chloroform:methanol:ammonium hydroxide, 30:10:1.

Pool the homogeneous fractions as determined by thin layer chromatography, concentrate and lyophilize to obtain 6'-N-ethylverdamicin.

EXAMPLE 7

6'-N-(δ-Aminobutyl)verdamicin

Dissolve 0.2 gm. of 1,3,2',3''-tetra-N-acetyl-5'-de-α-aminoethyl-5'-acetylverdamicin in a mixture of 5 ml. of ethanol, 5 ml. of water and 5 ml. of 1,4-diaminobutane. Stir the solution for 10 minutes, add 24 mg. of sodium borohydride and continue stirring for 30 minutes. Concentrate the solution to dryness in vacuo and dissolve the resultant residue in 20 ml. of 1N sodium hydroxide. Reflux the solution under nitrogen for 48 hours. Cool the solution and pass through 40 ml. of Amberlite IRC-50 ion exchange resin in the ammonium form and wash with water. Elute the product with 3% ammonium hydroxide solution and concentrate the eluate. Chromatograph the residue on 20 gm. silica gel using the system chloroform:methanol:ammonium hydroxide, 30:10:1.

Pool the homogenous fractions as determined by thin layer chromatography, concentrate and lyophilize to obtain 6'-N-(δ-aminobutyl)verdamicin.

EXAMPLE 8

6'-N-Alkylverdamicins

1. In a manner similar to that described in Example 6 react 1,3,2',3''-tetra-N-acetyl-5'-de-α-aminoethyl-5'-acetylverdamicin with an equivalent quantity of each of the following amines:

a. isopropylamine
b. cyclopropylmethylamine
c. phenylethylamine
d. ethanolamine
e. allylamine
e. allylamine
f. 4-acetamido-2-acetoxybutylamine
g. 4-(N-methylacetamido)-2-acetoxybutylamine and isolate the resultant products to obtain respectively:

h. 6'-N-isopropylverdamicin
i. 6'-N-cyclopropylmethylverdamicin
j. 6'-N-(2-phenylethyl)verdamicin
k. 6'-N-(β-hydroxyethyl)verdamicin
l. 6'-N-allylverdamicin
m. 6'-N-(β-hydroxy-δ-aminobutyl)verdamicin
n. 6'-N-[β-hydroxy-δ-(methylamino)butyl]verdamicin 2. In a manner similar to that described in Example 6, react the 1,3,2',3''-tetra-N-actyl-5'-de-α-aminoethyl-5'-acetylverdamicins of Example 2D with an excess quantity of the amines of Example 8 a-g to isolate the products of Example 8 h-n.

EXAMPLE 9

PREPARATION OF ACID ADDITION SALTS

A. Sulfate Salts (Sulfuric Acid Addition Salts)

Dissolve 5.0 gm. of 6'-N-ethylverdamicin in 25 ml. of water and adjust the pH of the solution to 4.5 with 1N sulfuric acid. Lyophilize to obtain 6'-N-ethylverdamicin sulfate.

B. Hydrochloride Salts

Dissolve 5.0 gm. of 6'-N-ethylverdamicin in 2.5 ml. of water . Acidify with 2N hydrochloric acid to pH 5. Lyophilize to obtain 6'-N-ethylverdamicin hydrochloride.

I claim:

1. A compound selected from the group consisting of 1,3,2',3''-tetra-N-X-6'-N-(2,4-dinitrophenyl)-sisomicin and 1,3,2',3''-tetra-N-X-6'-N-(2,4-dinitrophenyl)-verdamicin wherein X is a member selected from the group consisting of lower alkanoyl, benzoyl, nitrobenzoyl, methoxybenzoyl, toluyl, lower akoxycarbonyl, chloroacetyl and trichloroethoxycarbonyl.

2. A compound of claim 1 wherein X is acetyl.

3. A compound selected from the group consisting of 1,3,2',3''-tetra-N-X-5'-deaminomethyl-5'-formyl-sisimicin and 1,3,2',3''-tetra-N-X-5'-de-α-aminoethyl-5'-acetylverdamicin wherein X is a member selected from the group consisting of lower alkanoyl, benzoyl, nitrobenzoyl, methoxybenzoyl, toluyl, lower alkoxycarbonyl, chloroacetyl, and trichloroethoxycarbonyl.

4. A compound of claim 3 wherein X is acetyl.

5. A compound selected from the group consisting of 6'-N-Y-verdamicin wherein Y is an alkyl substituent selected from the group consisting of alkyl, alkenyl, cycloalkyl, hydroxyalkyl, aminoalkyl, alkylaminoalkyl, aminohydroxyalkyl and alkylaminohydroxyalkyl said alkyl substituent having up to 8 carbon atoms and when said alkyl substituent is substituted by both hydroxyl and amino functions, only one of said functions can be attached at any one carbon atom, and the pharmaceutically acceptable acid addition salts thereof.

6. A compound of claim 5 wherein Y is ethyl.

7. A compound of claim 5 wherein Y is δ-aminobutyl.

8. The process for preparing 6'-N-Y-sisomicin or 6'-N-Y-verdamicin wherein Y is an alkyl substituent selected from the group consisting of alkyl, alkenyl, cycloalkyl, hydroxyalkyl, aminoalkyl, alkylaminoalkyl, aminohydroxyalkyl and alkylaminohydroxyalkyl, said alkyl substituent having up to 8 carbon atoms and when said alkyl substituent is substituted by both hydroxy and amino functions, only one of said functons can be attached at any one carbon atoms, which comprises the reaction of 1,3,2',3''-tetra-N-X-6'-(2,4-dinitrophenyl) sisomicin or 1,3,2',3''-tetra-N-X-6'-(2,4-dinitrophenyl) verdamicin, respectively, wherein X is a member selected from the group consisting of lower alkanoyl, benzoyl, nitrobenzyl, methoxybenzoyl, toluyl, lower alkoxycarbonyl, chloroacetyl and trichloroethoxycarbonyl, in water with selenium dioxide, followed by reaction of the thereby formed 1,3,2',3'λ'-tetra-N-X-5'-deaminomethyl-5'-formylsisomicin or 1,3,2',3''-tetra-N-X-5'-de-α-aminoethyl-5'-acetylverdamicin, respectively, in a protic solvent with a primary amine having the formula Y—NH$_2$ wherein Y is as hereinabove defined, with a hydride donor reducing agent selected from the group consisting of sodium borohydride, lithium borohydride, potassium borohydride, lithium cyanoborohydride, sodium cyanoborohydride, morpholinoborane, dialkylaminoborane, tetraalkylammonium cyanoborohydride, thence reaction of the thereby formed N-protected-6'-N-Y-sisomicin or N-protected- 6'-N-Y-verdamicin intermediates with base to obtain 6'-N-Y-sisomicin or 6'-N-Y-verdamicin, respectively.

9. The process of claim 8 wherein X is acetyl.

* * * * *

UNITED STATES PATENT OFFICE
CERTIFICATE OF CORRECTION

Patent No. 3,997,524              Dated December 14, 1976

Inventor(s) Tattanahalli L. Nagabhushan

It is certified that error appears in the above-identified patent and that said Letters Patent are hereby corrected as shown below:

Column 1, line 51, "formula I: alkoxycarbonyl," should read ---following formula I:---. Column 4, line 38, "-1,3,2',3'-tetra-" should read ---1,3,2',3"-tetra---. Column 5, line 35, "-X-6"-" should read ---X-6'---. Column 7, line 6, "(OH⁻ cycle)," should read ---(OH⊖ cycle),---; Column 7, line 48, "(M .+)," should read ---(M.⁺),---. Column 9, line 46, "hydoxide" should read ---hydroxide Column 9, line 48, "-1,2,3',3"-" should read ---1,3,2',3"---; Column 9, line 65, "-5"-for-" should read ---5'-for---. Column 12, lines 35 and 36, "e. allylamine e. allylamine" should read ---e. allylamine---. Column 13, line 7, claim 1, "lower akoxy" should read ---lower alkoxy---; Column 13, line 12, claim 3, "sisimicin" should read ---sisomicin---. Column 14, line 7, claim 8, "atoms," should read ---atom,---; Column 14, lines 16 and 17, "-1,3,2',3'λ'-tetra-" should read ---1,3,2',3"-tetra---.

Signed and Sealed this

Fifteenth Day of March 1977

[SEAL]

Attest:

RUTH C. MASON
Attesting Officer

C. MARSHALL DANN
Commissioner of Patents and Trademarks